US011661389B2

(12) United States Patent
Petrov et al.

(10) Patent No.: US 11,661,389 B2
(45) Date of Patent: May 30, 2023

(54) FLUORINATED ALKOXYVINYL ETHERS AND METHODS FOR PREPARING FLUORINATED ALKOXYVINYL ETHERS

(71) Applicant: THE CHEMOURS COMPANY FC, LLC, Wilmington, DE (US)

(72) Inventors: Viacheslav A Petrov, Hockessin, DE (US); Mario Joseph Nappa, Leesburg, FL (US); Robert D Lousenberg, Wilmington, DE (US); Jonathan P Stehman, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 17/285,134

(22) PCT Filed: Oct. 10, 2019

(86) PCT No.: PCT/US2019/055506
§ 371 (c)(1),
(2) Date: Apr. 14, 2021

(87) PCT Pub. No.: WO2020/081334
PCT Pub. Date: Apr. 23, 2020

(65) Prior Publication Data
US 2021/0355057 A1 Nov. 18, 2021

Related U.S. Application Data

(60) Provisional application No. 62/745,733, filed on Oct. 15, 2018.

(51) Int. Cl.
*C07C 43/16* (2006.01)
*C07C 41/09* (2006.01)
*C09K 5/04* (2006.01)
*C11D 7/28* (2006.01)
*C11D 7/50* (2006.01)
*H01B 3/44* (2006.01)

(52) U.S. Cl.
CPC ............. *C07C 43/16* (2013.01); *C07C 41/09* (2013.01); *C09K 5/048* (2013.01); *C11D 7/28* (2013.01); *C11D 7/5022* (2013.01); *H01B 3/441* (2013.01)

(58) Field of Classification Search
CPC ......... C07C 43/17; C07C 41/05; C07C 41/09; C07C 41/06; C07C 43/15; C07C 43/16; C09K 5/04; C09K 5/048; C09K 5/10; C09K 2205/112; C11D 7/263; C11D 7/28; C11D 7/5018; C11D 7/5022; H01B 3/24; H01B 3/441; H01B 3/443; H01B 3/445

See application file for complete search history.

(56) References Cited

U.S. PATENT DOCUMENTS 5,350,497 A * 9/1994 Hung ...................... C07C 43/17
204/157.92
2010/0209600 A1 8/2010 Bartelt et al.

FOREIGN PATENT DOCUMENTS

| GB | 1206596 A | * | 9/1970 | ........... C07C 17/361 |
| GB | 1206596 A | | 9/1970 | |
| WO | 2010/094019 A2 | | 8/2010 | |
| WO | 2012/121749 A1 | | 9/2012 | |
| WO | WO-2017195070 A1 | * | 11/2017 | ............... C09K 5/04 |

OTHER PUBLICATIONS

R.D. Chambers et al., Journal of Fluorine Chemistry vol. 32, pp. 309-317. (Year: 1986).*
Hudlicky ("Synthesis of fluornated [alpha]-diketones and some intermediates," Journal of Fluorine Chemistry, vol. 18, No. 4, 1981, pp. 383-405) (Year: 1981).*
PCT International Search Report and Written Opinion dated Jan. 24, 2020 for PCT International Application No. PCT/US2019/055506.
Scherer, Kirby V., Jr. et al., A new synthetic approach to perfluorochemicals: liquid phase photofluorination with elemental fluorine. Part I, Journal of Fluorine Chemistry, 1990, pp. 47-65.

(Continued)

*Primary Examiner* — Matthew R Diaz

(57) ABSTRACT

An alkoxyvinyl ether is disclosed having the chemical structure $R_fC(OR)=CHR_f'$, wherein $R_f$ is an at least partially fluorinated functional group having at least one carbon atom, $R_f'$ is an at least partially fluorinated functional group having at least two carbon atoms, and R is a functional group. A method for preparing an alkoxyvinyl ether is disclosed, comprising $R_fCFHCFHR_f'+KOH/ROH \rightarrow R_fC(OR)=CHR_f'$, wherein $R_f$ is a perfluoro functional group, $R_f'$ is a perfluoro functional group, and R is an alkyl functional group. Another method for preparing an alkoxyvinyl ether is disclosed, comprising $R_fCF=CHR_f'+KOH/ROH \rightarrow R_fC(OR)=CHR_f'$, wherein $R_f$ is a perfluoro functional group, $R_f'$ is a perfluoro functional group, and R is an alkyl functional group.

14 Claims, No Drawings

(56) References Cited

OTHER PUBLICATIONS

Santini, G., et al., Some Unexpected Reactions of Perfluoroalkynyl—Magnesium Halides, Journal of Organometallic Chemistry, Jan. 1, 1975, pp C21-C24.

Studebaker, D.B. et al., Encapsulating bis(beta-ketoiminato) polyethers. Volatile, fluorine-free barium precursors for metal-organic chemical vapor deposition, Inorganic Chemistry, American Chemical Society, Jul. 24, 2000, pp. 3148-3157, vol. 39, No. 15, Easton, US.

Hudlicky, M., Synthesis of fluorinated [alpha]-diketones and some intermediates, Journal of Fluorine Chemistry, Oct. 1, 1981, pp. 383-405, vol. 18, No. 4, Blacksburg, Virginia.

Vasilevskaya T. N. et al, Reaction of Octafluoroacetophenone with Diazomethane, Journal of Organic Chemistry USSR, Jan. 1, 1970, pp. 1655-1657, Plenum Publ. Corp., US.

\* cited by examiner

FLUORINATED ALKOXYVINYL ETHERS AND METHODS FOR PREPARING FLUORINATED ALKOXYVINYL ETHERS

This application claims the benefit of Application No. 62/745,733, filed on Oct. 15, 2018. The disclosure of Application No. 62/745,733 is hereby incorporated by reference.

FIELD OF THE INVENTION

The present invention is directed to alkoxyvinyl ethers and methods for preparing alkoxyvinyl ethers. More particularly, the present invention is directed to fluorinated alkoxyvinyl ethers and methods for preparing fluorinated alkoxyvinyl ethers.

BACKGROUND OF THE INVENTION

Certain fluorinated materials of general structure $R_fC(OCH_3)=CFR_f'$ are known, and such materials may be prepared by the reaction of alcohols with a variety of perfluorinated olefins, such as F-pentene-2 (known as a commercial intermediate) or F-heptenes (known as waste stream components form the production of other materials). By way of example, the product of the reaction of F-heptenes with methanol (HFX-110) has been proposed for use as a solvent with low toxicity and low global warming potential.

However, to date there has been no disclosure in the scientific literature of fluorinated chemical species having the general structure of $R_fC(OR)=CHR_f'$, wherein $R_f'$ has at least two carbon atoms. Nor has there been any disclosure to date of a basic alcohol reaction pathway to prepare fluorinated chemical species having the general structure of $R_fC(OR)=CHR_f'$, wherein R is an alkyl functional group.

BRIEF DESCRIPTION OF THE INVENTION

In an exemplary embodiment, an alkoxyvinyl ether has the chemical structure $R_fC(OR)=CHR_f'$, wherein $R_f$ is an at least partially fluorinated functional group having at least one carbon atom, $R_f'$ is an at least partially fluorinated functional group having at least two carbon atoms, and R is a functional group.

In another exemplary embodiment, a method for preparing an alkoxyvinyl ether includes $R_fCFHCFHR_f'+KOH/ROH \rightarrow R_fC(OR)=CHR_f'$, wherein $R_f$ is a perfluoro functional group, $R_f'$ is a perfluoro functional group, and R is an alkyl functional group.

In another exemplary embodiment, a method for preparing an alkoxyvinyl ether includes $R_fCF=CHR_f'+KOH/ROH \rightarrow R_fC(OR)=CHR_f'$, wherein $R_f$ is a perfluoro functional group, $R_f'$ is a perfluoro functional group, and R is an alkyl functional group.

Another embodiment of the invention relates to any combination of the foregoing alkoxyvinyl ethers wherein:
  $R_f$ is a perfluoro functional group having at least one carbon atom;
  $R_f'$ is a perfluoro functional group having at least two carbon atoms; and
  R is a functional group having at least one carbon atom.

Another embodiment of the invention relates to any combination of the foregoing alkoxyvinyl ethers, wherein:
  $R_f$ is a perfluoroalkyl functional group;
  $R_f'$ is a perfluoroalkyl functional group having at least two carbon atoms; and
  R is an alkyl functional group.

Another embodiment of the invention relates to any combination of the foregoing alkoxyvinyl ethers, wherein:
  $R_f$ is a $C_{1-12}$ perfluoroalkyl functional group;
  $R_f'$ is a $C_{2-12}$ perfluoroalkyl functional group; and
  R is a $C_{1-12}$ alkyl functional group.

Another embodiment of the invention relates to any combination of the foregoing alkoxyvinyl ethers, wherein:
  $R_f$ is selected from the group consisting of $CF_3$, $C_2F_5$, n-$C_3F_7$, iso-$C_3F_7$, n-$C_4F_9$, sec-$C_4F_9$, iso-$C_4F_9$, and tert-$C_4F_9$;
  $R_f'$ is selected from the group consisting of $C_2F_5$, n-$C_3F_7$, iso-$C_3F_7$, n-$C_4F_9$, sec-$C_4F_9$, iso-$C_4F_9$, and tert-$C_4F_9$; and
  R is selected from the group consisting of $CH_3$, $C_2H_5$, n-$C_3H_7$, iso-$C_3H_7$, n-$C_4H_9$, sec-$C_4H_9$, iso-$C_4H_9$, and tert-$C_4H_9$.

Another embodiment of the invention relates to any combination of the foregoing alkoxyvinyl ethers, wherein:
  $R_f$ is a partially fluorinated functional group having at least one carbon atom;
  $R_f'$ is a partially fluorinated functional group having at least two carbon atoms; and
  R is a functional group having at least one carbon atom.

Another embodiment of the invention relates to any combination of the foregoing alkoxyvinyl ethers, wherein:
  $R_f$ is a perfluoro functional group having at least one carbon atom;
  $R_f'$ is a partially fluorinated functional group having at least two carbon atoms; and
  R is a functional group having at least one carbon atom.

Another embodiment of the invention relates to any combination of the foregoing alkoxyvinyl ethers, wherein:
  $R_f$ is a partially fluorinated functional group having at least one carbon atom;
  $R_f'$ is a perfluoro functional group having at least two carbon atoms; and
  R is a functional group having at least one carbon atom.

Another embodiment of the invention relates to any combination of the foregoing embodiments, wherein:
  $R_f$ is selected from the group consisting of $CF_3$, $CF_2H$, $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, and tert-$C_4F_9$, tert-$C_4F_8H$;
  $R_f'$ is selected from the group consisting of $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, and tert-$C_4F_9$, tert-$C_4F_8H$; and
  R is selected from the group consisting of $CH_3$, $C_2H_5$, n-$C_3H_7$, iso-$C_3H_7$, n-$C_4H_9$, sec-$C_4H_9$, iso-$C_4H_9$, and tert-$C_4H_9$.

Another embodiment of the invention relates to any combination of the foregoing embodiments wherein $R_f$ and $R_f'$ are the same.

Another embodiment of the invention relates to any combination of the foregoing embodiments, wherein $R_f$ and $R_f'$ are distinct.

Another embodiment of the invention relates to any combination of the foregoing embodiments, wherein the alkoxyvinyl ether is an E-isomer.

Another embodiment of the invention relates to any combination of the foregoing embodiments, wherein the alkoxyvinyl ether is a Z-isomer.

Another embodiment of the invention relates to any combination of the foregoing embodiments wherein the alkoxyvinyl ether is a mixture of E- and Z-isomers.

Another embodiment of the invention relates to any combination of the foregoing embodiments, wherein the chemical structure is $CF_3C(OCH_3)=CHC_2F_5$.

Another embodiment of the invention relates to any combination of the foregoing embodiments, wherein the chemical structure is $CF_3C(OC_2H_5)=CHC_2F_5$.

Another embodiment of the invention relates to any combination of the foregoing embodiments, wherein the chemical structure is $CF_3C(OC_3H_7)=CHC_2F_5$.

Another embodiment of the invention relates to any combination of the foregoing embodiments, wherein the chemical structure is $C_2F_5C(OCH_3)=CHC_3F_7$.

One embodiment of the invention relates to a method for preparing an alkoxyvinyl ether, comprising:

$$R_fCFHCFHR_f'+Base/ROH \rightarrow R_fC(OR)=CHR_f'$$

wherein:
 $R_f$ is a perfluoro functional group;
 $R_f'$ is a perfluoro functional group; and
 R is an alkyl functional group.

Another embodiment of the invention relates to a method for preparing an alkoxyvinyl ether, comprising:

$$R_fCF=CHR_f'+Base/ROH \rightarrow R_fC(OR)=CHR_f'$$

wherein:
 $R_f$ is a perfluoro functional group;
 $R_f'$ is a perfluoro functional group; and
 R is an alkyl functional group.

One embodiment of the invention relates to a solvent comprising any combination of the foregoing alkoxyvinyl ethers and at least one member selected from the group consisting of alcohols, ethers, tetrahydrofuran (THF), amides, or aromatic solvents.

Another embodiment of the invention relates to an alkoxyvinyl composition comprising:
 any combination of the foregoing alkoxyvinyl ethers;
 at least one solvent including at least one of alcohols, ethers, tetrahydrofuran (THF), amides, or aromatic solvents; and
 at least one base including at least one of KOH, NaOH, LiOH, $Ca(OH)_2$, tertiary amines, or alkoxides of alkali metals ROM (M=Li, Na, K, Cs).

Another embodiment of the invention relates to a process for transferring heat, comprising:
 providing an article;
 contacting the article with a heat transfer media;
 wherein the heat transfer media comprises any combination of the foregoing alkoxyvinyl ethers.

Another embodiment of the invention relates to the foregoing processes, wherein the boiling point of the alkoxyvinyl ether is between about 72 degrees Celsius and about 81 degrees Celsius.

Another embodiment of the invention relates to a process for treating a surface, comprising:
 providing a surface;
 contacting the surface with a treatment composition;
 wherein the surface includes a treatable material deposited thereon; and
 wherein the treatment composition comprises any of the foregoing combinations of alkoxyvinyl ethers.

Another embodiment of the invention relates to the foregoing processes, wherein the treatment composition substantially dissolves the treatable material.

Another embodiment of the invention relates to a process for forming a composition comprising:
 providing a solute;
 contacting the solute with a solvent;
 wherein the solvent comprises any combination of the foregoing alkoxyvinyl ethers.

Another embodiment of the invention relates to a process for providing electrical insulation, comprising:
 providing a first charged surface;
 providing a second charged surface;
 contacting the first charged surface and the second charged surface with a dielectric composition;
 wherein the dielectric composition comprises any combination of the foregoing alkoxyvinyl ethers.

Another embodiment of the invention relates to the foregoing processes, wherein the dielectric composition forms a continuous pathway between the first charged surface and the second charged surface.

The various embodiments of the invention can be used alone or in combinations with each other. Other features and advantages of the present invention will be apparent from the following more detailed description of the preferred embodiment, taken in conjunction with the accompanying drawings, which illustrate, by way of example, the principles of the invention.

DETAILED DESCRIPTION OF THE INVENTION

Provided are exemplary fluorinated alkoxyvinyl ethers and methods for preparing fluorinated alkoxyvinyl ethers. Embodiments of the present disclosure, in comparison to compositions of matter and methods not utilizing one or more features disclosed herein, include advantageous solvating properties, advantageous boiling point ranges, advantageous degreasing properties, advantageous heat transfer properties, decreased flammability, decreased atmospheric life time, increased polarity, or combinations thereof.

In some embodiments, the alkoxyvinyl ethers may find useful application as a cleaning agent or degreasing agent, a heat transfer media, a solvent, and/or a dielectric.

In one embodiment, an alkoxyvinyl ether has the following chemical structure:

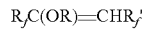
$$R_fC(OR)=CHR_f'$$

$R_f$ may be a partially fluorinated functional group or a perfluoro functional group, including, but not limited to, a partially fluorinated functional group having at least one carbon atom, a perfluoro functional group having at least one carbon atom, a partially fluorinated alkyl group, a perfluoroalkyl group, a $C_{1-12}$ partially fluorinated alkyl functional group, a $C_{1-12}$ perfluoroalkyl functional group, $CF_3$, $CF_2H$, $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, tert-$C_4F_9$, or tert-$C_4F_8H$.

$R_f'$ may be a partially fluorinated functional group or a perfluoro functional group, including, but not limited to, a partially fluorinated functional group having at least two carbon atoms, a perfluoro functional group having at least two carbon atoms, a partially fluorinated alkyl group having at least two carbon atoms, a perfluoroalkyl group having at least two carbon atoms, a $C_{2-12}$ partially fluorinated alkyl functional group, a $C_{2-12}$ perfluoroalkyl functional group, $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, tert-$C_4F_9$, or tert-$C_4F_8H$.

R is a functional group which may be, but is not limited to, a functional group having at least one carbon atom, an alkyl functional group, a $C_{1-12}$ alkyl functional group, $CH_3$, $C_2H_5$, n-$C_3H_7$, iso-$C_3H_7$, n-$C_4H_9$, sec-$C_4H_9$, iso-$C_4H_9$, or tert-$C_4H_9$.

The alkoxyvinyl ether may include any suitable combination of specific species of R, $R_f$, and $R_f'$ disclosed herein. $R_f$ and $R_f'$ may be identical or distinct from one another.

In one embodiment, $R_f$ is an at least partially fluorinated functional group having at least one carbon atom, $R_f'$ is an at least partially fluorinated functional group having at least two carbon atoms, and R is a functional group.

In another embodiment, $R_f$ is a perfluoro functional group having at least one carbon atom, $R_f'$ is a perfluoro functional group having at least two carbon atoms, and R is a functional group having at least one carbon atom.

In yet another embodiment, $R_f$ is a perfluoroalkyl functional group having at least one carbon atom, $R_f'$ is a perfluoroalkyl functional group having at least two carbon atoms, and R is an alkyl functional group.

In still another embodiment, $R_f$ is a $C_{1-12}$ perfluoroalkyl functional group, $R_f'$ is a $C_{2-12}$ perfluoroalkyl functional group, and R is a $C_{1-12}$ alkyl functional group.

In another embodiment, $R_f$ is selected from the group consisting of $CF_3$, $C_2F_5$, n-$C_3F_7$, iso-$C_3F_7$, n-$C_4F_9$, sec-$C_4F_9$, iso-$C_4F_9$, and tert-$C_4F_9$, $R_f'$ is selected from the group consisting of $C_2F_5$, n-$C_3F_7$, iso-$C_3F_7$, n-$C_4F_9$, sec-$C_4F_9$, iso-$C_4F_9$, and tert-$C_4F_9$, and R is selected from the group consisting of $CH_3$, $C_2H_5$, n-$C_3H_7$, iso-$C_3H_7$, n-$C_4H_9$, sec-$C_4H_9$, iso-$C_4H_9$, and tert-$C_4H_9$.

In yet another embodiment, $R_f$ is a partially fluorinated functional group having at least one carbon atom, $R_f'$ is a partially fluorinated functional group having at least two carbon atoms, and R is a functional group having at least one carbon atom.

In still another embodiment, $R_f$ is a perfluoro functional group having at least one carbon atom, $R_f'$ is a partially fluorinated functional group having at least two carbon atoms, and R is a functional group having at least one carbon atom.

In another embodiment, $R_f$ is a partially fluorinated functional group having at least one carbon atom, $R_f'$ is a perfluoro functional group having at least two carbon atoms, and R is a functional group having at least one carbon atom.

In yet another embodiment, $R_f$ is selected from the group consisting of $CF_3$, $CF_2H$, $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, and tert-$C_4F_9$, tert-$C_4F_8H$, $R_f'$ is selected from the group consisting of $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, and tert-$C_4F_9$, tert-$C_4F_8H$, and R is selected from the group consisting of $CH_3$, $C_2H_5$, n-$C_3H_7$, iso-$C_3H_7$, n-$C_4H_9$, sec-$C_4H_9$, iso-$C_4H_9$, and tert-$C_4H_9$.

The alkoxyvinyl ether may be an E-isomer, a Z-isomer, or a mixture of E- and Z-isomers.

The alkoxyvinyl ether may have any suitable chemical structure, including, but not limited to, $CF_3C(OCH_3)$=$CHC_2F_5$, $CF_3C(OC_2H_5)$=$CHC_2F_5$, $CF_3C(OC_3H_7)$=$CHC_2F_5$, and $C_2F_5C(OCH_3)$=$CHC_3F_7$.

In one embodiment, an alkoxyvinyl ether having the structure $R_fC(OR)$=$CHR_f'$ has a reduced flammability compared to an alkoxyvinyl ether having the structure $R_fC(OR)$=$CFR_f'$. By way of example, on the basis of calculated heats of formation, $CF_3C(OCH_3)$=$CHC_2F_5$ has a heat of combustion of about 2.08 kcal/g as compared to a heat of combustion of 2.58 kcal/g for $CF_3C(OCH_3)$=$CHCF_3$. The inventive alkoxyvinyl ethers can have a heat of combustion of less than about 2.1 kcal/g and, as a result, the inventive compounds can have a low or non-flammability rating.

In one embodiment, an alkoxyvinyl ether having the structure $R_fC(OR)$=$CHR_f'$ has a reduced atmospheric lifetime compared to an alkoxyvinyl ether having the structure $R_fC(OR)$=$CFR_f'$. The inventive alkoxyvinyl ethers can have an atmospheric lifetime ranging from about 10 to 200 days and, typically, less than 100 days.

In one embodiment, an alkoxyvinyl ether having the structure $R_fC(OR)$=$CHR_f'$ has an increased polarity compared to an alkoxyvinyl ether having the structure $R_fC(OR)$=$CFR_f'$. By way of example, on the basis of calculated dipole moments, $CF_3C(OCH_3)$=$CHC_2F_5$ has a dipole moment of 2.5460 D as compared to a dipole moment of 2.3965 D for $CF_3C(OCH_3)$=$CFC_2F_5$. The inventive alkoxyvinyl ethers can have a dipole moment of about 2 to about 5 D and in some cases about 2 to about 3D.

In one embodiment, a method for preparing an alkoxyvinyl ether, includes:

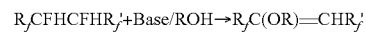

The method may include a prior step of:

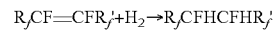

In another embodiment, a method for preparing an alkoxyvinyl ether, includes:

With respect to the methods for preparing the alkoxyvinyl ether: $R_f$ may be a partially fluorinated functional group or a perfluoro functional group, including, but not limited to, a partially fluorinated functional group having at least one carbon atom, a perfluoro functional group having at least one carbon atom, a partially fluorinated alkyl group, a perfluoroalkyl group, a $C_{1-12}$ partially fluorinated alkyl functional group, a $C_{1-12}$ perfluoroalkyl functional group, $CF_3$, $CF_2H$, $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, tert-$C_4F_9$, or tert-$C_4F_8H$; $R_f'$ may be a partially fluorinated functional group or a perfluoro functional group, including, but not limited to, a partially fluorinated functional group having at least one carbon atom, a perfluoro functional group having at least one carbon atom, a partially fluorinated alkyl group, a perfluoroalkyl group, a $C_{1-12}$ partially fluorinated alkyl functional group, a $C_{1-12}$ perfluoroalkyl functional group, $CF_3$, $CF_2H$, $C_2F_5$, $C_2F_4H$, n-$C_3F_7$, n-$C_3F_6H$, iso-$C_3F_7$, iso-$C_3F_6H$, n-$C_4F_9$, n-$C_4F_8H$, sec-$C_4F_9$, sec-$C_4F_8H$, iso-$C_4F_9$, iso-$C_4F_8H$, tert-$C_4F_9$, or tert-$C_4F_8H$; and R is a functional group which may be, but is not limited to, an alkyl functional group, a $C_{1-12}$ alkyl functional group, $CH_3$, $C_2H_5$, n-$C_3H_7$, iso-$C_3H_7$, n-$C_4H_9$, sec-$C_4H_9$, iso-$C_4H_9$, or tert-$C_4H_9$. The method may include any suitable combination of specific species of R, $R_f$, and $R_f'$ disclosed herein. $R_f$ and $R_f'$ may be identical or distinct from one another.

In one embodiment of the invention, at least one alkyoxyl vinyl ether can interact or react with elimination of HF. In a particular embodiment, the elimination of HF can produce at least one alkyoxyl vinyl ether with an additional double bond. In one particular embodiment at least one of the following groups can eliminate HF under certain reaction conditions: iso-$C_3F_6H$, n-$C_4F_8H$, sec-$C_4F_8H$, iso-$C_4F_8H$, or tert-$C_4F_8H$. Without wishing to be bound by any theory or explanation, it is believed that an excess amount of base can promote the HF elimination.

The base may be any suitable base, including, but not limited to, KOH, NaOH, LiOH, Ca(OH)$_2$, tertiary amines, and/or alkoxides of alkali metals ROM (M=Li, Na, K, Cs). The amount of base will be at least two moles per mole of reactant. If desired, the amount of reactant can be in excess of the molar amount of base and, unreacted material (if any) can be recycled in order to increase selectivity.

In some embodiments, the reaction composition may further include any suitable solvent, including, but not limited to, alcohols, ethers (e.g., glymes, diethyl ether, methyl-t-butyl ether), tetrahydrofuran (THF), amides, and/or aromatic solvents (e.g., benzene, toluene, xylenes). The amount of solvent can range from about 0.5 to about 500 moles per mole of reactant and, in some cases, about 5 to about 100 moles of solvent.

In some embodiments, the reaction may be performed in the absence of solvent, under phase-transfer catalysis (PTC) conditions. Suitable phase transfer catalysts include, but are not limited to, tetraalkylammonium salts, phosphonium salts, and/or crown ethers. The amount of catalyst can range from about 0.1 to about 50 mole percent relative to the reactant and, in some cases, about 5 to 15 mole percent.

In some embodiments, the reaction may be performed at a temperature of at least −20 degrees Celsius, at least 0 degrees Celsius, at least 10 degrees Celsius, at least 20 degrees Celsius, at least 25 degrees Celsius, at least 30 degrees Celsius, at least 40 degrees Celsius, less than 110 degrees Celsius, less than 100 degrees Celsius, less than 90 degrees Celsius, less than 80 degrees Celsius, less than 70 degrees Celsius, less than 60 degrees Celsius, less than 50 degrees Celsius, and combinations thereof. The reaction pressure can be conducted at atmospheric pressure and, if desired, the pressure can be increased to greater than atmospheric pressure (e.g., about 1 to about 100 atmospheres).

The alkoxyvinyl ether may be useful in various applications. In an embodiment, the alkoxyvinyl ether may be used in accordance with convention equipment and methods to transfer heat. The process may include providing an article and contacting the article with a heat transfer media including the alkoxyvinyl ether. In some embodiments, the article may include electrical equipment (e.g., circuit board, computer, display, semiconductor chip, or transformer), a heat transfer surface (e.g., heat sink), or article of clothing (e.g., a body suit).

In another embodiment, the alkoxyvinyl ether may be used in a process for treating a surface. The process may include providing a surface having a treatable material deposited thereon and contacting the surface with a treatment composition including the alkoxyvinyl ether. In some embodiments, the treatment composition may substantially dissolve the treatable material. While the inventive alkoxyvinyl ethers can be used in any suitable equipment and methods, examples of such methods are disclosed by WO2012/121749 and WO2010/094019; the disclosure of which is hereby incorporated by reference.

In another embodiment, the alkoxyvinyl ether may be used in a process for forming a composition. The process includes providing a solute and contacting the solute with a solvent including the alkoxyvinyl ether. In some embodiments, the alkoxyvinyl ether may substantially dissolve the solute. Except for water, the inventive alkoxyvinyl ethers are miscible with conventional organic as well as fluorinated solvents.

In an embodiment, the alkoxyvinyl ether may be used in conventional equipment and in a process for providing electrical insulation. The process includes providing a first charged surface, providing a second charged surface, and contacting the first charged surface and the second charged surface with a dielectric composition including the alkoxyvinyl ether. In some embodiments, the dielectric composition forms a continuous pathway between the first charged surface and the second charged surface. In some embodiments, the first charged surface and the second charged surface may be substantially submerged in the dielectric composition.

The following Examples are provided to illustrate certain aspects of the invention and shall not limit the scope of the appended claims.

EXAMPLES

Example 1. Reaction of $CF_3CFHCFHC_2F_5$ (I) with $CH_3OH/KOH$

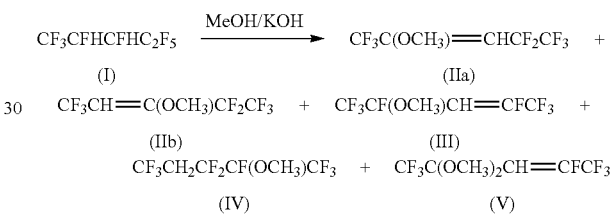

A solution of 240 g (4.27 mol) of KOH in 1400 mL of methanol was placed in a 3 L round-bottomed flask equipped with reflux condenser, thermocouple, addition funnel and magnetic stir bar. The flask was immersed in ice cooling bath. Vertrel® XF (1,1,1,2,2,3,4,5,5,5-decafluoropentane, I, 504 g, 2 mol) was added dropwise to the cooled solution, while maintaining the internal temperature below 10° C. (~3 hours). The reaction mixture was allowed to warm to ambient temperature overnight. The next morning the reaction mixture was washed in portions with a large excess of ice water in a separatory funnel. The fluorous layers were collected, combined, and washed with a saturated solution of sodium bicarbonate (1 L×2), dried with $MgSO_4$ and filtered to yield 448 g of crude product. Crude products from three consecutive runs were combined (total 1085 g) and distilled at atmospheric pressure, using a 16-inch-long distillation column. Distillation data and the composition of the fractions is shown in Table 1.

TABLE 1

| | Distillation of Crude Reaction Mixture | | | | | | | |
|---|---|---|---|---|---|---|---|---|
| | Weight | Pot Temp | Head Temp | Composition (wt %) | | | | |
| Fraction | (g) | (° C.) | (° C.) | (I) | (IIa)(IIb) | (III) | (IV) | (V) |
| 1 | 12 | 71.6-72 | 56-59.8 | 67 | 33 | — | — | — |
| 2 | 11 | 72-72.1 | 59.8-60.6 | 63 | 37 | — | — | — |
| 3 | 11 | 72.1-72.1 | 62-66.1 | 31 | 68 | — | — | — |
| 4 | 22 | 72.1-72.5 | 66.1-66.5 | 24 | 76 | — | — | — |
| 5 | 27 | 72.5-72.7 | 66.5-69.1 | 40 | 60 | — | — | — |
| 6 | 22 | 72.7-72.7 | 69.1-71.9 | 17 | 83 | — | — | — |
| 7 | 20 | 72.7-72.9 | 71.9-72 | 4.5 | 95.1 | — | — | — |

TABLE 1-continued

Distillation of Crude Reaction Mixture

| Fraction | Weight (g) | Pot Temp (° C.) | Head Temp (° C.) | Composition (wt %) | | | | |
|---|---|---|---|---|---|---|---|---|
| | | | | (I) | (IIa)(IIb) | (III) | (IV) | (V) |
| 8 | 157 | 73.2-73.3 | 72-73.2 | 2.9 | 96.8 | — | — | — |
| 9 | 133 | 73.3-73.3 | 73.2-73.2 | — | 99.4 | — | — | — |
| 10 | 164 | 73.3-73.8 | 73.2-73.2 | — | 98.5 | 1.0 | — | — |
| 11 | 111 | 73.8-74.4 | 73.2-73.3 | — | 98.7 | 0.8 | — | — |
| 12 | 117 | 74.8-75.9 | 73.3-73.5 | — | 99.4 | 0.6 | — | — |
| 13 | 124 | 75.9-80.8 | 73.5-73.6 | — | 99.3 | 0.6 | — | — |
| 14 | 58 | 81-96 | 73.6-75 | — | 95 | 3.7 | 1 | — |
| 15 | 17 | 96-116 | 75-76.2 | — | 89 | 7.8 | 2.7 | — |
| 16 | 18 | 116-130 | 76.2-80.4 | — | 68 | 17.1 | 14.7 | — |
| POT | 44 | | | | 4 | 5 | 27 | 47 |

Combined fractions 8-13 (806 g total, yield 55%) were analyzed by NMR and shown to be a ~99% pure mixture of compounds IIa and IIb in ratio 85:15

Compound IIa:
$^1$H NMR (CDCl$_3$, J, Hz): 3.98 (3H, s), 5.74 (1H, q, 8.4), ppm
$^{19}$F NMR (CDCl$_3$, J, Hz): −55.34 (3F, d, 8.1), −83.23 (3F, t, 1.5), −119.34 (2F, s) ppm Compound IIb:
$^1$H NMR (CDCl$_3$, δ, J, Hz): δ 3.92 (3H, s), 5.57 (1H, t, 13.3) ppm
$^{19}$F NMR (CDCl$_3$, J, Hz): −69.42 (3F, s), −85.78 (3F, t, 2.5), −110.70 (2F, dt, 13.8, 2.5) ppm Compound III:
$^1$H NMR (CDCl$_3$, J, Hz): 3.58 (3H, s), 5.62 (1H, dd, 28.1, 15.6) ppm
$^{19}$F (CDCl$_3$, J, Hz): −60.66 (3F, m, 9.9, 4.5), −80.36 (3F, d, 8.8), −118.90 (1F, tm, 28.1), −127.24 (1F, dd, 28.1, 15.3) ppm Compound IV:
$^1$H NMR (CDCl$_3$, J, Hz): 2.84 (2H, m), 3.62 (3H, q, 1.2) ppm
$^{19}$F (CDCl$_3$, J, Hz): −73.41 (3F, d, 9.9), −83.86 (3F, t, 4.5), −124.71 (2F, A:B q, 286.0), −130.45 (1F, m, 9.1) ppm Compound V:
$^1$H NMR (CDCl$_3$, J, Hz): 3.41 (6H, s), 5.48 (1H, d, 33.2) ppm
$^{19}$F (CDCl$_3$, J, Hz): −73.24 (3F, d, 9.3), −78.23 (3F, d, 6.8), −120.87 (1F, dm, J$_d$=33.2) ppm Example 2. Reaction of CF$_3$CFHCFHC$_2$F$_5$ with CF$_3$CH$_2$OH/KOH

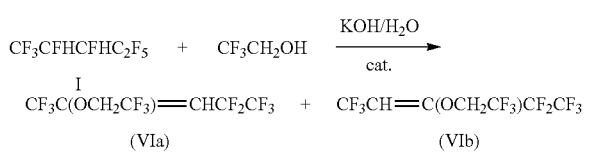

A 500 mL 3-neck round bottomed flask was equipped with an addition funnel, thermocouple, and reflux condenser. Under a nitrogen blanket, 200 mL of 45 wt % KOH/water solution was added, along with 2 g of catalyst—tetrabutylammonium bromide (TBAB, phase transfer catalyst). This mixture was cooled in an ice bath down to ~5° C. and 50 g (~36 mL, 0.5 mol) of trifluoroethanol was added dropwise over 30 mins period at 10° C. Addition of trifluoroethanol was followed by slow addition of 125 g (0.5 mol) of I at 5-10° C. (~30 min). The reaction mixture was slowly brought to ambient temperature (~4 hrs). After stirring at ambient temperature for an additional ~3 hrs, the reaction mixture was poured into 500 mL of water, fluorous layer separated, washed with water, dried over MgSO$_4$, filtered and distilled using a Vigreux column. 87 g (yield 56%) of fraction b.p. 95-98° C. was isolated. The fraction contained isomers VIa and VIb in a ratio of 72:25, respectively and about 3% of other isomeric products.

Compound VIa:
$^1$H NMR (CDCl$_3$, J, Hz): 4.39 (2H, q, 7.7) 5.98 (1H, q, 7.6), ppm
$^{19}$F NMR (CDCl$_3$, J, Hz): δ−57.32 (3F, dq, 7.5, 1.7), −75.19 (3F, t, 7.8), −83.16 (3F, d, 0.7), −118.83 (2F, s) ppm Compound VIb:
$^1$H NMR (CDCl$_3$, J, Hz): δ 5.80 (1H, t, 12.9), 4.36 (2H, q, 7.9) ppm
$^{19}$F NMR (CDCl$_3$, J, Hz): −69.20 (3F, s), −75.1 (3F, t, 7.6), −85.54 (3F, t, 2.3), −112.23 (2, F dm, 12.9, 2.1) ppm Example 3. Reaction of CF$_3$CFHCFHC$_2$F$_5$ with CH$_3$CH$_2$OH/KOH

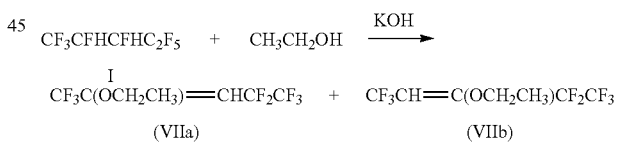

Using the procedure described above in Example 1, 126 g (0.5 mol) of I, was added to a solution of 70 g (1.07 mol) of KOH in 400 ml of ethanol. The resulting crude product isolated after washing reaction mixture with water, drying, filtration and distillation yielded 94.4 g (yield 73%) of material with b.p. 85-89° C., which was found to be a mixture of VIIa and VIIb in a ratio 75:25, containing 3% isomeric material (NMR and GC/MS).

Compound VIIa:
$^1$H NMR (CDCl$_3$, J, Hz): 1.36 (3H, t, 7.4), 4.19 (2H, q, 7.4), 5.74 (1H, q, 8.0) ppm
$^{19}$F NMR (CDCl$_3$, J, Hz): −56.34 (3F, dt, 8.1, 2.2), −83.18 (3F, t, 1.9), −119.23 (2F, s) ppm Compound VIIb:
$^1$H NMR (CDCl$_3$, J, Hz): 1.35 (3H, t, 7.3), 4.14 (2H, q, 7.3), 5.74 (1H, t, 12.8) ppm $^{19}$F NMR (CDCl$_3$, J, Hz): −69.58 (3F, s), −85.81 (3F, t, 2.5), −111.27 (2F, dm, J$_d$=13.8) ppm Example 4. Reaction of CF$_3$CFHCFHC$_2$F$_5$ with (CH$_3$)$_2$CHOH/KOH

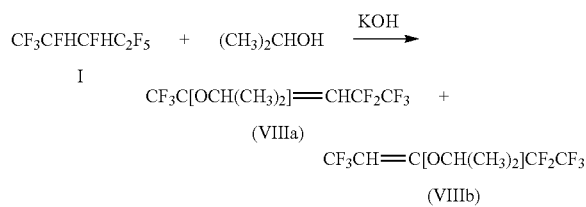

Following the procedure described above in Example 1. Compound I (126 g, 0.5 mol) was added to a solution of 70 g (1.07 mol) of KOH in 400 ml of iso-propanol. The isolated crude product was distilled to yield 79 g (yield 61%) of a fraction with b.p. 98-99° C., containing a mixture of VIIa and VIIb in a ratio of ~70:30, containing 3% of other isomeric material (NMR, GC/MS).

Compound VIIIa:
$^1$H NMR (CDCl$_3$, J, Hz): 1.31 (6H, d, 6.0), 4.63 (1H, quint., 6.0), 5.76 (1H, q, 8.0) ppm
$^{19}$F NMR ((CDCl$_3$, J, Hz): −57.54 (3F, dt, 8.0, 2.1), −83.00 (3F, t, 1.9), −117.99 (2F, s) ppm Compound VIIIb:
$^1$H NMR (CDCl$_3$, J, Hz): 1.31 (6H, d, 6.0), 4.56 (1H, quint., 6.0), 5.56 (1H, t, 13.0) ppm
$^{19}$F NMR (CDCl$_3$, J, Hz): −68.38 (3F, s), −85.57 (3F, t, 2.5), −111.55 (2F, dq, 13.0, 2.2) ppm Example 5. Reaction of C$_3$F$_7$CH=CFC$_2$F$_5$/ C$_3$F$_7$CF=CHC$_2$F$_5$ with MeOH/KOH

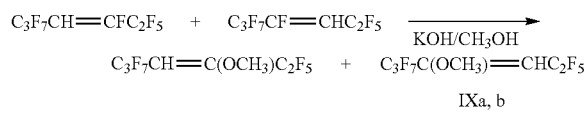

Following the procedure described above in Example 1. The olefin (mixture of C$_3$F$_7$CH=CFC$_2$F$_5$ and C$_3$F$_7$CF=CHC$_2$F$_5$ in ratio ~ 1:1) was added to a solution of KOH (20 g, 0.36 mol) in 300 ml of MeOH. After work up 105 g of crude product was isolated and distilled to yield 61.5 g (yield 46%), of a fraction with b.p. 107-110° C., containing a mixture of IXa, IXb, and isomeric material in ratio 45:40:15 (GC/MS, NMR)

Major isomer (content—45% in a mixture):
$^1$H NMR (CDCl$_3$, J, Hz): 3.96 (3H, t, 1.2), 5.66 (1H, t, 14.5) ppm
$^{19}$F NMR (CDCl$_3$, J, Hz): −81.14 (3F, t, 9.5), −85.02 (3F, t, 1.9), −109.06 (2F, dm, J$_d$=14.5), −116.39 (2F, q, 9.5), −127.05 (2F, s) ppm Minor isomer (content—40% in a mixture):
$^1$H NMR (CDCl$_3$, J, Hz): 3.92 (3H, t, 1.2), 5.73 (1H, t, 14.0) ppm
$^{19}$F NMR (CDCl$_3$, J, Hz): δ−80.78 (3F, t, 9.2), −83.55 (3F, m), −107.16 (2F, quint., 11.0), −118.55 (2F, s), −128.09 (2F, s) ppm While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An alkoxyvinyl ether having the following chemical structure:

$$R_fC(OR)=CHR_f'$$

wherein:
R$_f$ is CF$_3$;
R$_f'$ is C$_2$F$_5$; and
R is CH$_3$.

2. The alkoxyvinyl ether of claim 1, wherein the alkoxyvinyl ether is an E-isomer.

3. The alkoxyvinyl ether of claim 1, wherein the alkoxyvinyl ether is a Z-isomer.

4. The alkoxyvinyl ether of claim 1, wherein the alkoxyvinyl ether is a mixture of E- and Z-isomers.

5. A method for preparing an alkoxyvinyl ether, comprising:

$$R_fCFHCFHR_f'+Base/ROH→R_fC(OR)=CHR_f'$$

wherein:
R$_f$ is a perfluoro functional group;
R$_f'$ is a perfluoro functional group; and
R is an alkyl functional group.

6. A method for preparing an alkoxyvinyl ether, comprising:

$$R_fCF=CHR_f'+Base/ROH→R_fC(OR)=CHR_f'$$

wherein:
R$_f$ is a perfluoro functional group;
R$_f'$ is a perfluoro functional group; and
R is an alkyl functional group.

7. An alkoxyvinyl composition comprising:
the alkoxyvinyl ether of claim 1;
a solvent including at least one of alcohols, ethers, tetrahydrofuran (THF), amides, or aromatic solvents; and
a base including at least one of KOH, NaOH, LiOH, Ca(OH)$_2$ tertiary amines, or alkoxides of alkali metals.

8. A process for transferring heat, comprising:
providing an article;
contacting the article with a heat transfer media;
wherein the heat transfer media comprises the alkoxyvinyl ether of claim 1.

9. The process of claim 8, wherein the boiling point of the alkoxyvinyl ether is between 72 degrees Celsius and 81 degrees Celsius.

10. A process for treating a surface, comprising:
providing a surface;
contacting the surface with a treatment composition;
wherein the surface includes a treatable material deposited thereon; and
wherein the treatment composition comprises the alkoxyvinyl ether of claim 1.

11. The process of claim 10, wherein the treatment composition substantially dissolves the treatable material.

12. A process for forming a composition comprising:
providing a solute;

contacting the solute with a solvent;
wherein the solvent comprises the alkoxyvinyl ether of claim 1.

13. A process for providing electrical insulation, comprising:
providing a first charged surface;
providing a second charged surface;
contacting the first charged surface and the second charged surface with a dielectric composition;
wherein the dielectric composition comprises the alkoxyvinyl ether of claim 1.

14. The process of claim 13, wherein the dielectric composition forms a continuous pathway between the first charged surface and the second charged surface.

* * * * *